US012797593B2

(12) United States Patent
Sieracki et al.

(10) Patent No.: US 12,797,593 B2

(45) Date of Patent: Nov. 17, 2026

(54) ON-DEVICE SELECTIVE REMOVAL OF IMPURITIES IN CLEANING FLUID

(71) Applicant: CareFusion 2200, Inc., San Diego, CA (US)

(72) Inventors: Nathan Sieracki, San Diego, CA (US); Fanqing Meng, San Diego, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 515 days.

(21) Appl. No.: 18/269,189

(22) PCT Filed: Nov. 11, 2021

(86) PCT No.: PCT/US2021/058968

§ 371 (c)(1),
(2) Date: Jun. 22, 2023

(87) PCT Pub. No.: WO2022/139973

PCT Pub. Date: Jun. 30, 2022

(65) Prior Publication Data

US 2024/0131313 A1 Apr. 25, 2024
US 2024/0226520 A9 Jul. 11, 2024

Related U.S. Application Data

(60) Provisional application No. 63/129,361, filed on Dec. 22, 2020.

(51) Int. Cl.

| | |
|---|---|
| ***A61M 35/00*** | (2006.01) |
| ***A61L 2/18*** | (2026.01) |
| ***A61L 101/32*** | (2006.01) |

(52) U.S. Cl.

CPC ............. *A61M 35/006* (2013.01); *A61L 2/18* (2013.01); *A61L 2101/32* (2020.08); *A61M 2205/02* (2013.01)

(58) Field of Classification Search

CPC ............ A61M 35/006; A61M 2205/02; A61M 35/003; A61M 2205/0205; A61L 2/18; A61L 2101/32; A61L 2/16; C07D 473/04

(Continued)

(56) References Cited

U.S. PATENT DOCUMENTS

| | | | |
|---|---|---|---|
| 5,308,180 | A | 5/1994 | Pournoor et al. |
| 7,422,388 | B2 | 9/2008 | Tufts et al. |

(Continued)

FOREIGN PATENT DOCUMENTS

| | | | |
|---|---|---|---|
| CN | 105813683 | A | 7/2016 |
| JP | 2009-526624 | A | 7/2009 |

(Continued)

OTHER PUBLICATIONS

Yang et al. "Adsorption and correlations of selected aromatic compounds on a KOH-activated carbon with large surface area." Science of The Total Environment 618 (Mar. 15, 2018) 1677-1684. Abstract, Figure 1; Table 1.

*Primary Examiner* — David J Walczak

(74) *Attorney, Agent, or Firm* — ArentFox Schiff LLP and Care Fusion

(57) ABSTRACT

A cleaning device having a body containing a cleaning fluid, an application member in selective fluid communication with the body via a fluid path, and a first selectively permeably element provided along the fluid path, the first selectively permeable element being configured to selectively interact with one or more selected components of the cleaning fluid sufficient to remove the one or more selected components from the cleaning fluid as the cleaning fluid travels along the fluid path, and wherein selective interaction between the first selectively permeable element and the one or more selected components includes at least a physical (Continued)

interaction. Also disclosed in methods of making and using the cleaning devices described herein.

20 Claims, 1 Drawing Sheet

(58) Field of Classification Search
USPC ................ 401/132–134, 196, 205, 263, 264; 544/273, 112, 242, 265, 267, 309, 311
See application file for complete search history.

(56) References Cited

U.S. PATENT DOCUMENTS

| | | | | |
|---|---|---|---|---|
| 7,993,066 | B2 | 8/2011 | Flores et al. | |
| 8,118,766 | B2 | 2/2012 | Davis et al. | |
| 8,858,484 | B2 | 10/2014 | Casey et al. | |
| 8,911,771 | B2 | 12/2014 | Vanek et al. | |
| 9,629,990 | B2 | 4/2017 | Law | |
| 9,999,757 | B2 | 6/2018 | Chiang et al. | |
| 12,151,925 | B2 * | 11/2024 | May | B67B 7/92 |
| 2007/0231051 | A1 | 10/2007 | Flores et al. | |
| 2010/0226706 | A1 * | 9/2010 | Flores | A61M 35/006 401/133 |
| 2012/0298558 | A1 | 11/2012 | Calabro et al. | |
| 2014/0081221 | A1 | 3/2014 | Mcdonald et al. | |
| 2018/0161561 | A1 | 6/2018 | Shiozaki et al. | |
| 2018/0333566 | A1 | 11/2018 | Follman et al. | |
| 2019/0170543 | A1 | 6/2019 | Rothenberg et al. | |

FOREIGN PATENT DOCUMENTS

| | | | |
|---|---|---|---|
| JP | 2019-516747 | A | 6/2019 |
| TW | 202000301 | A | 1/2020 |

* cited by examiner

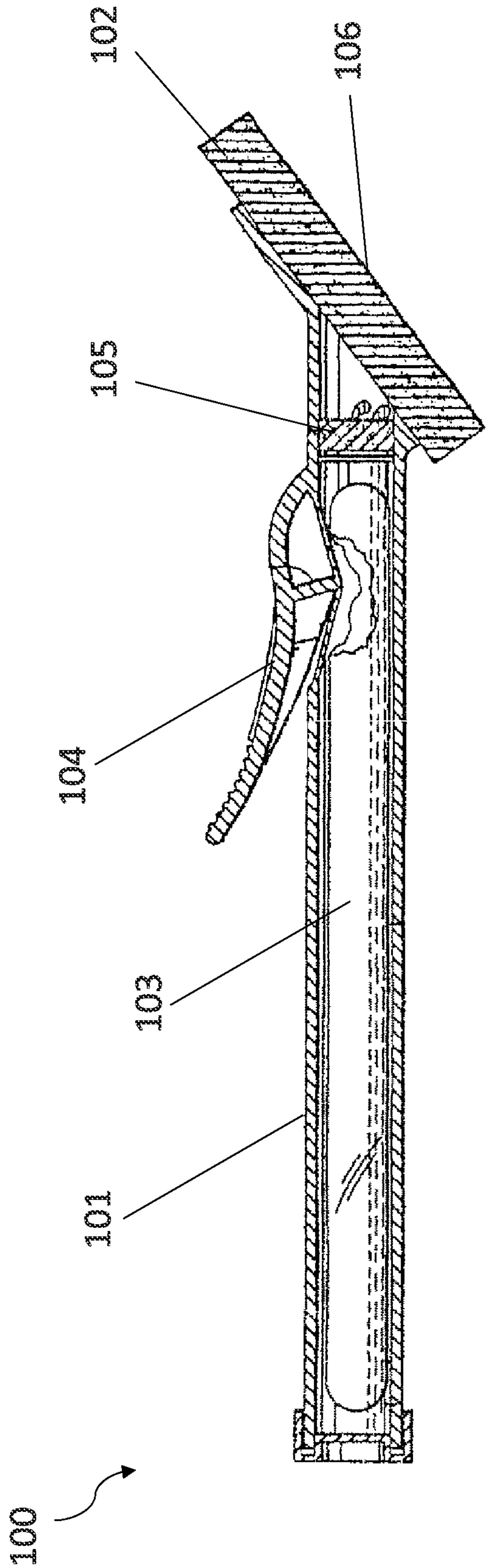
102
106
105
104
103
101
100

ON-DEVICE SELECTIVE REMOVAL OF IMPURITIES IN CLEANING FLUID

CROSS-REFERENCE TO RELATED APPLICATION

This application is a National Stage Entry of PCT/US2021/058968, filed Nov. 11, 2021, which claims priority to U.S. Provisional Application No. 63/129,361, filed on Dec. 22, 2020, the contents of which is expressly incorporated by reference herein in its entirety.

TECHNICAL FIELD

The present disclosure is directed to cleaning devices configured to concurrently and/or successively remove one or more selected components from a cleaning fluid contained in the cleaning device and apply the cleaning fluid to a surface.

BACKGROUND

In the medical setting, antiseptics are often used to prepare surfaces such as patient skin and medical device surfaces for medical procedures. One common antiseptic used in medical settings is chlorhexidine gluconate, which exhibits a strong affinity for binding to skin, has a high level of antibacterial activity, and prolonged residual effects. However, chlorhexidine gluconate is also associated with the unfavorable and undesired impurity 4-chloroaniline (PCA, CAS 106-47-8) from its thermal degradation. Other impurities associated with chlorhexidine gluconate include N-(4-Chlorophenyl)-N'-[6-[[(cyanoamino)iminomethyl]amino]hexyl]imidodicarbonimidic Diamide (CAS; 152504-08-0); [[6-[[[(4-Chlorophenyl) carbamimdoyl] carbamimidoyl]amino]hexyl]carbamimidoyl]urea Dihydrochloride (CAS 1308292-89-8); N-(4-chlorophenyl)guanidine; N-(4-Chloro-phenyl)-guanidine (45964-97-4); 1-(4-Chlorophenyl)urea (140-38-5), N-(4-Chlorophenyl)-14-[(4-chlorophenyl)amino]-3,12,14-triimino-2,4,11,13-tetraazatetradecanamide (CAS 1381962-77-1); (1E)-2-[6-[[amino-[(E)-[amino(anilino)methylidene]amino]methylidene]amino]hexyl]-1- [amino-(4-chloroanilino)methylidene]guanidine (CAS 152504-12-6); and N-[6-[(Aminoiminomethyl)amino]hexyl]-N'-(4-chlorphenyl)-imidodicarbonimidic diamide (CAS 152504-10-4). Other antiseptics used in the medical setting, such as alexidine, olanexidine, octenidine, and quaternary amine compounds, are similarly associated with unfavorable impurities. For example, impurities associated with octenidine dihydrochloride include 1-chloro-10(N-octyl-4-aminopyridinium)-decane-hydrochloride, N[1-[10-(4-amino-1(4H)-pyridinyl)-decyl]-4(1H)-pyridinylidene]-octanamine-dihydrochloride, acetone, N,N-dimethylformamide, 1,10 dichlordecane, and N-octyl-4-pyridinamine.

In current practice, specified impurity levels are generally controlled via climatic specifications on product labels. However, there still remains a need in the art for devices capable of purifying antiseptic solutions in situ, particularly organic chlorhexidine gluconate-containing formulations, via a single pass at the time of device actuation.

SUMMARY

The present disclosure is directed to cleaning devices configured to concurrently and/or successively remove one or more selected components from a cleaning fluid and apply the cleaning fluid to a surface. In particular, the cleaning device may comprise a body in selective fluid communication with an application member via a fluid path, wherein the application member is configured to apply the cleaning fluid to a surface. The fluid path may comprise at least one selectively permeable element configured to selectively remove the one or more selected components from a cleaning fluid as the cleaning fluid passes therethrough.

BRIEF DESCRIPTION OF THE DRAWINGS

FIG. 1 shows an example cleaning device according to aspects of the present disclosure.

DETAILED DESCRIPTION

The present disclosure is directed to cleaning devices configured to concurrently and/or successively remove one or more selected components from a cleaning fluid and apply the cleaning fluid to a surface. In particular, the cleaning device may comprise a body in selective fluid communication with an application member via a fluid path, wherein the application member is configured to apply the cleaning fluid to a surface. The fluid path may comprise at least one selectively permeable element configured to selectively remove the one or more selected components from a cleaning fluid as the cleaning fluid passes therethrough.

As used herein, the term “cleaning device” is any device configured to clean a surface as described herein. As used herein, “to clean” means to perform one or more cleaning operations, such one or more disinfection steps and/or one or more antiseptic action steps.

According to some aspects, the cleaning device may be an applicator. As used herein, the term “applicator” refers to a device having at least a body and an application member, wherein the body is configured to house a cleaning fluid and is in selective fluid communication with the application member such that cleaning fluid may be selectively delivered from the body to the application member via a fluid path. The application member may be a component of the applicator configured to apply the cleaning fluid to a surface, such as a foam, a felt, or any suitable material that allows the application of cleaning fluid to a surface external to the applicator. Non-limiting examples of materials useful for the application member include those described in U.S. Pat. No. 7,993,066, the contents of which are incorporated by reference herein. For example, the application member may comprise an open-celled foam material, such as a hydrophilic polyester-polyurethane foam.

According to some aspects, the body may comprise a handle portion, that is, the portion of the cleaning device by which the cleaning device is controlled by a user. It should be understood that in the case wherein the body comprises a handle portion, the body as described herein may alternatively be referred to as a handle portion.

For example, FIG. 1 shows one non-limiting example of an applicator 100 according to aspects of the present disclosure, applicator 100 having a body 101 and an application member 102. According to some aspects, body 101 of applicator 100 may house one or more ampoules and/or similar containers 103 in which cleaning fluid may be contained prior to application to a surface. Applicator 100 may optionally comprise an actuator 104 configured to actuate the applicator, wherein actuation of actuator 104 corresponds to body 101 being provided in fluid communication with application member 102 via a fluid path as described herein.

Non-limiting example applicators that may be used according to the present disclosure may be found, for example, in Applicant's U.S. Pat. Nos. 5,690,958; 6,536,975; 7,993,066; 8,708,983; 8,899,859; 9,119,946; 9,572,967; 9,757,551; 9,968,764; 10,076,648; 10,549,078; and 10,813,892, the disclosures of which are incorporated herein by reference in their entirety.

In one non-limiting example, the one or more cleaning operations according to the present disclosure may comprise one or more disinfection steps. As used herein, the term "disinfect" means destroying, inactivating, or significantly reducing the concentration of at least a portion of microorganisms present on an inanimate surface and/or reducing or preventing the growth of microorganisms on an inanimate surface. Example inanimate surfaces include, but are not limited, work surfaces in a medical setting, surfaces of medical devices, and combinations thereof. Additionally, or alternatively, the one or more cleaning operations according to the present disclosure may comprise one or more antiseptic action steps. As used herein, performing an "antiseptic action" means destroying, inactivating, or significantly reducing the concentration of at least a portion of microorganisms present on a human or animal surface and/or reducing or preventing the growth of microorganisms on a human or animal surface. Example human and animal surfaces include, but are not limited to, skin, wound surfaces, hair follicles, mucous membranes, and combinations thereof.

In one example, the one or more disinfection and/or antiseptic action steps may comprise applying a cleaning fluid comprising a biocide and/or a biostat to a surface sufficient to destroy, inactivate, or significantly reduce the concentration of at least a portion of microorganisms present on the surface and/or to reduce or prevent the growth of microorganisms on the surface. As used herein, the term "biocide" refers to a chemical agent that inactivates microorganisms as described herein. As used herein, the term "biostat" refers to a chemical agent that reduces and/or prevents the growth of microorganisms as described herein. It should be understood that in some instances, a chemical agent may function as a biocide and a biostat.

Example biocides and/or biostats according to the present disclosure include antibiotics, antiseptics, and disinfectants. As used herein, an "antibiotic" is a naturally occurring or synthetic organic substance which inhibits or destroys selective bacteria or other microorganisms, generally at low concentrations. As used herein, an "antiseptic" is a biocide and/or biostat that destroys or inhibits the growth of microorganisms in or on living tissue. As used herein, a "disinfectant" is a biocide and/or biostat that destroys or inhibits the growth of microorganisms in or on an inanimate surface.

Non-limiting examples of biocides and/or biostats according to the present disclosure include alcohols, aldehydes, anilides, biguanides, diamidines, halogen-releasing agents, silver compounds, peroxygens, phenols, bis-phenols, halophenols, quaternary ammonium compounds, combinations thereof, and solutions thereof.

According to some aspects, the cleaning fluid may be a cleaning solution comprising a biocide and/or a biostat and a solvent. For example, the cleaning fluid may be an antiseptic solution comprising an antiseptic and a solvent. According to some aspects, the cleaning solution is an aqueous solution. As used herein, the term "aqueous solution" refers to a solution wherein the solvent comprises at least a majority of water. According to some aspects, the cleaning solution is an organic solution. As used herein, the term "organic solution" refers to a solution wherein the solvent comprises at least a majority of an organic component, such as an alcohol.

According to some aspects, the antiseptic may comprise a cationic molecule (i.e., a molecule having a positive charge), such as a cationic surfactant or a cationic biguanide derivative (i.e., a compound derived from biguanide). According to some aspects, the antiseptic may comprise a bis-(dihydropyridinyl)-decane derivative (i.e., a compound derived from bis-(dihydropyridinyl)-decane). According to some aspects, the antiseptic may comprise an octenidine salt and/or a chlorhexidine salt. Non-limiting examples of antiseptics useful according to the present discourse include octenidine dihydrochloride, chlorhexidine gluconate, and a combination thereof.

According to some aspects, the concentration of each biocide and/or biostat in the cleaning solution, or alternatively the total concentration of biocides and/or biostats in the cleaning solution, may be from about 0.0001% to about 2.0% w/v, optionally from about 0.01% to about 1% w/v, optionally from about 0.1% to about 0.4% w/v. According to some aspects, the concentration of each biocide and/or biostat in the cleaning solution, or alternatively the total concentration of biocides and/or biostats in the cleaning solution, may be from about 0.0001% to about 0.4% w/v, and optionally from about 0.1% to about 0.2% w/v. According to some aspects, the concentration of antiseptic in the antiseptic solution may be from about 0.5% to about 2.0% w/v, and optionally about 2.0% w/v.

According to some aspects, the solvent may comprise an organic solvent, such as an alcohol, an organosulfur compound, a ketone, or combinations thereof. Non-limiting examples of alcohols include methanol, ethanol, propanol, such as n-propanol and/or isopropanol, and combinations thereof. One non-limiting example of a ketone includes acetone. One non-limiting example of an organosulfur compound includes dimethyl sulfoxide (DMSO). According to some aspects, the concentration of organic solvent in the cleaning solution may be from about 50% to about 90% v/v, optionally from about 70% to about 80% v/v, and optionally about 70% v/v. According to some aspects, the concentration of alcohol in the cleaning solution may be from about 10% to about 50% v/v, and optionally from about 20% to about 30% v/v.

According to some aspects, the solvent may comprise water. According to some aspects, the concentration of water in the cleaning solution may be from about 10% to about 50% v/v, and optionally from about 20% to about 30% v/v. According to some aspects, the concentration of water in the cleaning solution may be from about 50% to about 90% v/v, and optionally from about 70 to about 80% v/v.

According to some aspects, the cleaning solution may further comprise a film-forming polymer. Non-limiting examples of film-forming polymers include acrylate polymers (such as acrylamide polymers, octylacrylamide polymers, methacrylate polymers), carboxyacrylate polymers, and polymers having dimethylaminoethyl methacrylate, butyl methacrylate, and methyl methacrylate side groups. The concentration of film-forming polymer may be varied depending on the particular solvent and biocide and/or biostat present in the cleaning solution.

According to some aspects, the concentration of film-forming polymer in the cleaning solution may be from about 0.1% to about 5% w/v, optionally from about 0.2% to about 3% w/v, optionally from about 0.5% to about 2.0% w/v, and optionally from about 0.75% to about 2.5% w/v.

Example acrylate polymers include, but are not limited to, DERMACRYL® AQF (2-propenoic acid, 2-methyl-, polymer with butyl 2-propenoate and methyl 2-methyl-2-propenoate), DERMACRYL® 79P (2-propenoic acid, 2-methyl-, 2-methylpropyl ester, polymer with 2-propenoic acid and N-(1,1,3,3tetramethylbutyl)-2-propenamide), each manufactured by Akzo Nobel Coatings Inc, and EUDRAGIT® E PO (poly(butyl methacylate-co-(2-dimethylaminoethyl) methacrylate-co-methyl methacrylate) manufactured by Evonik Industries. DERMACRYL® 79P is a hydrophobic, high molecular weight carboxylated acrylic copolymer. EUDRAGIT® E PO is a cationic copolymer based on dimethylaminoethyl methacrylate, butyl methacrylate, and methyl methacrylate According to some aspects, the cleaning solution may further comprise a tinting agent. In some non-limiting examples, the tinting agent may comprise an anionic tinting agent, such as an anionic dye. The anionic dye may be any dye suitable for medical use, such as dyes approved by the Food and Drug Administration for use in food, drugs, and/or cosmetics (i.e., "D&C" or "FD&C" dyes). Example anionic dyes include, but are not limited to, FD&C Blue No. 1 (Brilliant Blue FCF), FD&C Blue No.2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, and combinations thereof. Combinations may be implemented to arrive at a particular color. For example, an orange tint may comprise both FD&C Red No. 40 and D&C Yellow No. 8.

According to some aspects, the concentration of tinting agent in the cleaning solution may be from about 0.01% to about 0.15% w/v, optionally from about 0.03% to about 0.12% w/v, and optionally from about 0.05% to about 0.09% w/v.

According to some aspects, the cleaning solution may include one or more plasticizers. The plasticizer may be an ester of an organic acid, for example, such as triethyl citrate or dibutyl sebacate. The concentration of plasticizer in the antiseptic solution may be from about 0.05% to about 2% w/v, optionally from about 0.75% to about 1.5%, and optionally from about 0.1% to about 1% w/v.

According to some aspects, the antiseptic solution may be the solution used in ChloraPrep™ applicators, which comprises about 2% w/v chlorhexidine gluconate in a solvent comprising about 70% v/v isopropyl alcohol and about 30% v/v water.

The cleaning devices of the present disclosure comprise at least one selectively permeable element provided along the fluid path as described herein. It should be understood that the "fluid path" as described herein refers to the path originating at a source of the cleaning fluid contained by the cleaning device (e.g., one or more ampoules and/or similar containers as described herein) and terminating at a surface-contacting portion of the application member. For example, FIG. 1 shows an example selectively permeable element 105 positioned in body 101 such that, upon actuation, a cleaning fluid released from ampoule 103 (e.g., by fracturing frangible ampoule 103 by actuator 104) passes through selective permeable element 105 as it travels along the fluid path toward application member 102. In this way, applicator 100 is configured to, upon actuation, successively remove one or more selected components (e.g., one or more impurities) from a cleaning fluid via at least selectively permeable element 105 and apply the cleaning fluid to a surface via application member 102.

In the example shown in FIG. 1, selectively permeable element 105 may comprise a fluid metering device, such as a pledget, configured to at least partially control and/or direct the flow of the cleaning fluid from ampoule 103 to application member 102. However, selectively permeable element 105 is not necessarily limited as such.

It should also be understood that the present disclosure is not particularly limited to the example shown in FIG. 1. In particular, the selectively permeable element as described in relation to FIG. 1 may be provided at any point along the fluid path between, for example, ampoule 103 and a surface-contacting portion 106 of application member 102. In one non-limited example, the selectively permeable element may be provided as a component of application member 102. In this way, the applicator may be configured to, upon actuation, concurrently remove one or more selected components (e.g., one or more impurities) from a cleaning fluid via the selectively permeable element comprised by the application member and apply the cleaning fluid to a surface via the application member. Additionally or alternatively, the cleaning device may further comprise a second, third, fourth, or more selectively permeable element as described herein, wherein each of the selectively permeable elements is the same or different from at least one other selectively permeable element comprised by the cleaning device.

The at least one selectively permeable element according to the present disclosure is configured to selectively remove one or more selected components from a cleaning fluid passing therethrough. According to some aspects, one or more selected components may comprise one or more impurities. As used herein, the term "impurity" refers to an undesired substance in a composition. It should be understood that one or more impurities may be present in an initial composition and/or may be formed after a certain period of shelf life of a composition. For example, one or more impurities may be formed via degradation of one or more components of the composition, such as the biocide and/or biostat. Sources of degradation include, but are not limited to, oxidation, racemization, hydrolysis reactions, condensation reactions, composition component interactions, and environmental stimuli, such as visible light, ultraviolet light, moisture, heat (including heat from a sterilization process), and changes in pH.

Example impurities as described herein include, but are not limited to, impurities understood in the art to be associated with a cleaning solution as described herein. In one non-limiting example wherein the cleaning solution comprises chlorhexidine gluconate, impurities may include 4-chloroaniline (PCA); N-(4-Chlorophenyl)-N'-[6-[[(cyanoamino)iminomethyl]amino]hexyl]imidodicarbonimidic Diamide; [[6-[[[(4-Chlorophenyl) carbamimdoyl] carbamimidoyl]amino]hexyl]carbamimidoyl]urea Dihydrochloride; N-(4-chlorophenyl)guanidine; N-(4-Chloro-phenyl)-guanidine (45964-97-4); 1-(4-Chlorophenyl)urea; N-(4-Chlorophenyl)-14-[(4-chiorophenyl)amino]-3,12,14-triimino-2,4,11,13-tretraazatetradecanamide; (1E)-2-[6-[[amino-[(E)-[amino(anilino)methylidene]amino] methylidene]amino]hexyl]-1-[amino-(4-chloroanilino) methylidene]guanidine; N-[6-[(Aminoiminomethyl)amino] hexyl]-N'~(4-chlorophenyl)-imidodicarbonimidic diamide; and combinations thereof. In other non-limiting examples wherein the antiseptic solution comprises octenidine dihydrochloride, impurities may include 1-chloro-10(N-octyl-4-aminopyridinium)-decane-hydrochloride; N[1-[10-(4-amino-1(4H)-pyridinyl)-decyl]-4(1H)-pyridinylidene]-octanamine-dihydrochloride; acetone; N,N-dimethylformamide, 1,10 dichlordecane; N-octyl-4-pyridinamine; and combinations thereof.

Additionally or alternatively, one or more of the selected components as described herein may comprise one or more impurity complexes formed from one or more impurities as described herein and one or more resin particles. In one non-limiting example, the one or more resin particles may comprise particles of a selectively permeable microporous material as will be described herein. For example, the one or more impurity complexes may comprise a complex formed from PCA that has physically and/or chemically interacted with activated carbon particle(s).

According to some aspects, selective removal of the one or more selected components from the cleaning fluid comprises a selective interaction between the selectively permeable element and the one or more selected components sufficient to bind, entrap, and/or otherwise immobilize the one or more selected components within the selectively permeable element while allowing other components of the cleaning fluid to pass through the selectively permeable element.

According to some aspects, the selective interaction between the selectively permeable element and the one or more selected components may comprise a physical interaction, a chemical interaction, or a combination thereof. For example, the selectively permeable element may be configured to chemically interact with one or more selected components as described herein. The chemical interaction may comprise any chemical interaction known in the art, including covalent bonding, acid-base reaction, non-covalent interactions (e.g., hydrogen bonding, electrostatic, rr-effects, van der Waals forces, hydrophobic effects), and combinations thereof.

Additionally, or alternatively, the selectively permeable element may be configured to physically interact with one or more selected components via entrapment of one or more selected component molecules in one or more pores of the selectively permeable element.

According to some aspects, the selectively permeable element may be configured to provide at least one physical and/or chemical interaction with at least one selected component comprised by a cleaning fluid, optionally at least two different physical and/or chemical interactions, optionally at least three different physical and/or chemical interactions, and optionally at least four different physical and/or chemical interactions. In one non-limiting example, the selectively permeable element may comprise a porous component having a plurality of pores with an average size sufficient to entrap one or more selected component molecules as described herein. Additionally, or alternatively, the selectively permeable element may be configured to interact with the one or more selected component molecules via pi-pi interactions.

According to some aspects, the selective permeability element may be configured to selectively remove at least a portion of the one or more components from the cleaning fluid without compromising the function of the cleaning device. Examples of compromising effects include, but are not limited to, an unacceptable change in cleaning fluid flow rate along the fluid path, an unacceptable change in drain time (i.e., the time required for the cleaning fluid to partially or completely drain from the one or more ampoules and/or similar containers after actuation), and/or an unacceptable change in wetting time (i.e., the time required for an application member to be wetted by the cleaning fluid after actuation). Additionally or alternatively, the selectively permeable element may be configured such that it does not compromise the titer of one or more unselected components of the cleaning fluid, such as any of the components of an antiseptic solution as described herein.

According to some aspects, the selectively permeable element may comprise a selectively permeable porous material, such as a resin and/or a film comprising a selectively permeable porous material. According to some aspects, the selectively permeable porous material comprises a plurality of pores having an average pore size configured to entrap one or more selected component molecules as described herein. In some non-limiting examples, the selectively permeable porous material may comprise a selectively permeable microporous material, a selectively permeable mesoporous material, and/or a selectively permeable macroporous material. As used herein, the term "microporous material" refers to a material having a plurality of pores, wherein at least a portion of the plurality of pores has an average pore size (alternatively referred to herein as the average pore diameter) of about 2 nm or less. As used herein, the term "mesoporous material" refers to a material having a plurality of pores, wherein at least a portion of the plurality of pores has an average pore size of between about 2 and 50 nm. As used herein, the term "macroporous material" refers to a material having a plurality of pores, wherein at least a portion of the plurality of pores has an average pore size of at least about 50 nm. A microporous material may be selected in order to provide the general contribution to the internal surface area to absorb and trap the targeted impurities, while materials with a different average pore size (e.g., a mesoporous and/or a macroporous material) may additionally or alternatively be selected to provide kinetics pathways. Non-limiting examples of selectively permeable microporous materials according to the present disclosure include, but are not limited to, zeolites, activated carbon, and combinations thereof. In one non-limiting example wherein the one or more selected components comprises PCA, the activated carbon and/or a zeolite may have an average pore size of between about 1 and 10 Å, optionally between about 3 and 7 Å, and optionally about 5 Å.

Additionally, the activated carbon and/or zeolite may be configured to chemically interact with one or more selected components as described herein. For example, the activated carbon and/or zeolite may be functionalized with one or more functional groups that selectively interact with one or more selected component molecules as described herein. Example functional groups as described herein include, but are not limited to, organic functional groups.

As used herein, the term "activated carbon" refers to carbon that has been processed to have small, low-volume pores. In particular, activated carbon is specially treated carbon with a high degree of microporosity characterized by the presence of a high content of low-volume pores. With different treatments, the selected activated carbon candidates may demonstrate a pH from 3 to 7, with a molasses number EUR from 90 to 800. Additionally or alternatively, the total surface area may be in the range of 1500 $m^2/g$ to 1850 $m^2/g$ and/or the tamped apparent density may be from 180 kg/m3 to 460 $kg/m^3$. The particle size distribution with $D_5$ may be in the range of 4 μm to 6 μm, with $D_{50}$ in the range of 16 to 23 μm and Do in the range of 44 μm to 69 μm.

According to some aspects, the activated carbon according to the present disclosure comprises powdered activated carbon. It should be understood that activated carbon may be classified on the basis of one or more properties as described herein, including but not limited to pH, chloride content, molasses number EUR, methylene blue adsorption, surface area (B.E.T.), tamped apparent density, particle size distribution ($D_5$, $D_{50}$, and/or $D_{90}$), and/or ash content.

In one non-limiting example, the selectively permeable microporous material according to the present disclosure may comprise an activated carbon having a pH of between about 3.0 and 8.0, optionally between about 3.0 and 7.0, optionally between about 3.0 and 5.0, optionally between about 6.0 and 8.0, optionally between about 6.5 and 7.5, and optionally about 7.0.

Additionally or alternatively, the selectively permeable microporous material according to the present disclosure may comprise an activated carbon having an iodine number of between 1500 and 1700, optionally between about 1550 and 1650, and optionally about 1600. Additionally or alternatively, the selectively permeable microporous material according to the present disclosure may comprise an activated carbon having an iodine number of between 1200 and 1500, optionally between about 1300 and 1450, optionally about 1300, and optionally about 1400. Additionally or alternatively, the selectively permeable microporous material according to the present disclosure may comprise an activated carbon having an iodine number of between 600 and 1100, optionally between about 700 and 1000, optionally between about 800 and 900, and optionally about 850.

Additionally or alternatively, the selectively permeable microporous material according to the present disclosure may comprise an activated carbon having a molasses number EUR between about 500 and 1000, optionally between about 500 and 700, optionally between about 700 and 900, optionally about 800, or optionally about 600. Additionally or alternatively, the selectively permeable microporous material according to the present disclosure may comprise an activated carbon having a molasses number EUR between about 1 and 800, optionally between about 90 and 800, optionally between about 100 and 400, optionally between 200 and 300, optionally about 280, and optionally about 250. Additionally or alternatively, the selectively permeable microporous material according to the present disclosure may comprise an activated carbon having a molasses number EUR between about 50 and 150, optionally between about 60 and 140, optionally between 70 and 130, optionally between about 80 and 120, optionally about 90, and optionally about 115.

Additionally or alternatively, the selectively permeable microporous material according to the present disclosure may comprise an activated carbon having a methyl blue absorption of between about 30 and 50 g/100 g, optionally between about 30 and 40 g/100 g, optionally between about 30 and 40 g/100 g, optionally about 38 g/100 g, and optionally about 34 g/100 g. Additionally or alternatively, the selectively permeable microporous material according to the present disclosure may comprise an activated carbon having a methyl blue absorption of between about 30 and 50 g/100 g, optionally between about 40 and 50 g/100 g, optionally between about 40 and 45 g/100 g, and optionally about 42 g/100 g. Additionally or alternatively, the selectively permeable microporous material according to the present disclosure may comprise an activated carbon having a methyl blue absorption of between about 10 and 30 g/100 g, optionally between about 15 and 25 g/100 g, optionally between about 15 and 20 g/100 g, and optionally about 18 g/100 g.

Additionally or alternatively, the selectively permeable microporous material according to the present disclosure may comprise an activated carbon having a particle size distribution ($D_5$) of between about 1 and 10 μm, optionally between about 1 and 5 μm, optionally between about 2 and 5 μm, optionally between about 3 and 5 μm, and optionally about 4 μm. Additionally or alternatively, the selectively permeable microporous material according to the present disclosure may comprise an activated carbon having a particle size distribution ($D_5$) of between about 5 and 10 μm, optionally between about 5 and 9 μm, optionally between about 5 and 8 μm, optionally between about 5 and 7 μm, optionally between about 4 and 7 μm, and optionally about 6 μm.

Additionally or alternatively, the selectively permeable microporous material according to the present disclosure may comprise an activated carbon having a particle size distribution ($D_{50}$) of between about 10 and 30 μm, optionally between about 15 and 25 μm, optionally about 16 μm, optionally about 20 μm, and optionally about 23 μm. Additionally or alternatively, the selectively permeable microporous material according to the present disclosure may comprise an activated carbon having a particle size distribution ($D_{50}$) of between about 16 and 23 μm.

Additionally or alternatively, the selectively permeable microporous material according to the present disclosure may comprise an activated carbon having a particle size distribution ($D_{90}$) of between about 40 and 80 μm, optionally between about 50 and 70 μm, optionally between about 55 and 75 μm, and optionally about 60 μm. Additionally or alternatively, the selectively permeable microporous material according to the present disclosure may comprise an activated carbon having a particle size distribution ($D_{90}$) of between about 40 and 120 μm, optionally between about 50 and 110 μm, optionally between about 50 and 100 μm, optionally between about 60 and 100 μm, and optionally between about 70 and 90 μm. Additionally or alternatively, the selectively permeable microporous material according to the present disclosure may comprise an activated carbon having a particle size distribution ($D_{90}$) of about 44 μm, optionally about 60 μm, optionally about 69 μm, and optionally about 80 μm. Additionally or alternatively, the selectively permeable microporous material according to the present disclosure may comprise an activated carbon having a particle size distribution ($D_{90}$) of between about 44 and 69 μm.

Additionally or alternatively, the selectively permeable microporous material according to the present disclosure may comprise an activated carbon having an ash content of between about 1 and 6 mass-%, optionally between about 1 and 5 mass-%, optionally between about 1 and 4 mass-%, optionally between about 1 and 3 mass-%, optionally about 3 mass-%, and optionally about 2 mass-%. Additionally or alternatively, the selectively permeable microporous material according to the present disclosure may comprise an activated carbon having an ash content of between about 1 and 9 mass-%, optionally between about 2 and 8 mass-%, optionally between about 3 and 7 mass-%, optionally between about 4 and 6 mass-%, and optionally about 5 mass-%.

Additionally or alternatively, the selectively permeable microporous material according to the present disclosure may comprise an activated carbon having a total surface area (B.E.T.) of between about 1400 and 2000 $m^2/g$, optionally between about 1500 and 1850 $m^2/g$, optionally between about 1400 and 1800 $m^2/g$, optionally between about 1400 and 1600 $m^2/g$, optionally between about 1600 and 1800 $m^2/g$, optionally about 1500 $m^2/g$, optionally about 1650 $m^2/g$, optionally about 1700 $m^2/g$, and optionally about 1850 $m^2/g$. Additionally or alternatively, the selectively permeable microporous material according to the present disclosure may comprise an activated carbon having a total surface area (B.E.T.) of between about 400 and 1400 $m^2/g$, optionally between about 500 and 1300 $m^2/g$, optionally between about 600 and 1200 $m^2/g$, optionally between about 700 and 1100 $m^2/g$, optionally between about 800 and 1000 $m^2/g$, and optionally about 900 $m^2/g$.

Additionally or alternatively, the selectively permeable microporous material according to the present disclosure may comprise an activated carbon having a tamped apparent density of between about 400 and 500 $kg/m^3$, optionally between about 400 and 470 $kg/m^3$, optionally between about 400 and 420 $kg/m^3$, optionally between about 450 and 470 $kg/m^3$, optionally about 410 $kg/m^3$, or optionally about 460 $kg/m^3$. Additionally or alternatively, the selectively permeable microporous material according to the present disclosure may comprise an activated carbon having a tamped apparent density of between about 100 and 600 $kg/m^3$, optionally between about 100 and 500 $kg/m^3$, optionally between about 180 and 460 $kg/m^3$, optionally between about 300 and 400 $kg/m^3$, and optionally about 350 $kg/m^3$. Additionally or alternatively, the selectively permeable microporous material according to the present disclosure may comprise an activated carbon having a tamped apparent density of between about 50 and 300 $kg/m^3$, optionally between about 100 and 300 $kg/m^3$, optionally between about 100 and 200 $kg/m^3$, optionally between about 200 and 300 $kg/m^3$, optionally about 180 $kg/m^3$, and optionally about 260 $kg/m^3$.

Additionally or alternatively, the selectively permeable microporous material according to the present disclosure may comprise an activated carbon having a chloride content (acid ext.) of between about 0.01 and 2 mass-%, optionally between about 0.01 and 1 mass-%, optionally between about 0.01 and 0.1 mass-%, and optionally about 0.05 mass-%.

Additionally or alternatively, the selectively permeable microporous material according to the present disclosure may comprise an activated carbon having an absorptive power (dyes) of between about 0.5 and 2.5 mL, optionally between about 1 and 2 mL, and optionally about 1.6 mL. Additionally or alternatively, the selectively permeable microporous material according to the present disclosure may comprise an activated carbon having an absorptive power (dyes) of between about 0.01 and 4 mL, optionally between about 1 and 3 mL, and optionally about 2 mL.

Additionally or alternatively, the selectively permeable microporous material according to the present disclosure may comprise a powdered activated carbon having the specifications as provided in Table 1 below.

TABLE 1

| Example Specifications for Powdered Activated Carbon | |
|---|---|
| Per USP 37 | |
| Microbial Limit | Passing |
| Reaction (pH) | Neutral |
| Acid soluble substances | Max. 3.5 (mass-%) |
| Chloride | Max. 0.2 (mass-%) |
| Sulphate | Max 0.2 (mass-%) |
| Sulphide | Passing |
| Cyanogen Compounds | Passing |
| Uncarbonized Constituents | Passing |
| Loss on Drying | Max. 15.0 (mass-%) |
| Residue in ignition | Max. 4.0 (mass-%) |
| Absorptive Power: Alkaloids | Passing |
| Absorptive Power: Dyes | Min. 0.7 (mL) |
| Other | |
| Methylene Blue Absorption | Min. 38 (g/100 g) |
| Acid Soluble Matter | Max. 1.0 (mass-%) |
| Calcium (acid ext.) | Max. 200 (mg/kg) |
| Iron (acid ext.) | Max. 200 (mg/kg) |
| Magnesium (acid ext.) | Max. 200 (mg/kg) |
| Moisture (as packed) | Max. 10 (mass-%) |

Additionally or alternatively, the selectively permeable microporous material according to the present disclosure may comprise an activated carbon having the specifications as provided in Table 2 below.

TABLE 2

| Example Specifications for Powdered Activated Carbon | |
|---|---|
| Per USP 37 | |
| Microbial Limit | Passing |
| Reaction (pH) | Neutral |
| Acid soluble substances | Max. 3.5 (mass-%) |
| Chloride | Max. 0.2 (mass-%) |
| Sulphate | Max 0.2 (mass-%) |
| Sulphide | Passing |
| Cyanogen Compounds | Passing |
| Uncarbonized Constituents | Passing |
| Loss on Drying | Max. 15.0 (mass-%) |
| Residue in ignition | Max. 4.0 (mass-%) |
| Absorptive Power: Alkaloids | Passing |
| Absorptive Power: Dyes | Min. 0.7 (mL) |
| Other | |
| Methylene Blue Absorption | Min. 28 (g/100 g) |
| Acid Soluble Matter | Max. 1.0 (mass-%) |
| Moisture (as packed) | Max. 10 (mass-%) |

Additionally or alternatively, the selectively permeable microporous material according to the present disclosure may comprise an activated carbon having the specifications as provided in Table 3 below.

TABLE 3

| Example Specifications for Powdered Activated Carbon | |
|---|---|
| Per USP 37 | |
| Microbial Limit | Passing |
| Reaction (pH) | Neutral |
| Acid soluble substances | Max. 3.5 (mass-%) |
| Chloride | Max. 0.2 (mass-%) |
| Sulphate | Max 0.2 (mass-%) |
| Sulphide | Passing |
| Cyanogen Compounds | Passing |
| Uncarbonized Constituents | Passing |
| Loss on Drying | Max. 15.0 (mass-%) |
| Residue in ignition | Max. 4.0 (mass-%) |
| Absorptive Power: Alkaloids | Passing |
| Absorptive Power: Dyes | Min. 0.7 (mL) |
| Other | |
| Methylene Blue Absorption | Min. 14 (g/100 g) |
| Acid Soluble Matter | Max. 1.0 (mass-%) |
| Moisture (as packed) | Max. 10 (mass-%) |

Example activated carbon materials suitable for use according to the present disclosure include, but are not limited to, NORIT®A SUPRA, NORIT B®, and NORITS KB-EV from Cabot Corporation.

Additionally, or alternatively, the selectively permeable porous material as described herein may be configured to physically and/or chemically interact with one or more impurity complexes as described herein. For example, in the case wherein the one or more impurity complexes is formed from PCA that has physically and/or chemically interacted with activated carbon particles, the selectively permeable porous material may comprise a plurality of pores having an average pore size configured to entrap one or more impurity complexes. Additionally, or alternatively, the selectively permeable porous material may be functionalized with one or more functional groups that selectively interact with one or more impurity complexes as described herein. For example, functionalization of a carbon surface with an organic weak acid functional group would be expected to sensitize the surface toward capture of PCA, due to the relatively low pKa value of the aniline nitrogen atom in PCA in comparison to other amines impurities in the mixture that are quantitatively protonated (and thus, unavailable for weak acid interaction/capture) at physiological pH.

In the non-limiting example shown in FIG. 1, selectively permeable element 105 may comprise a pledget as described herein, wherein the pledget comprises a selectively permeable porous material as described herein, such as a selectively permeable microporous material. Additionally or alternatively, selectively permeable element 105 may comprise a pledget having one or more selectively permeable porous materials provided as a coating on at least one surface or being embedded in the matrix thereof. For example, selectively permeable element 105 may comprise a pledget formed from any porous material that allows liquid to flow therethrough, such as a hydrophobic or hydrophilic foam or felt material. In this example, the porous material may be at least partially coated or embedded with one or more selectively permeable porous materials as described herein. Example hydrophobic or hydrophilic foam or a felt materials useful for a pledget according to the present disclosure include, but are not limited to, those described in U.S. Pat. No. 7,993,066. In one example, selectively permeable element 105 may comprise a polyurethane foam or felt, such as a hydrophilic ester polyurethane foam, with at least one outer surface coated or embedded by a selectively permeable porous material as described herein.

Additionally or alternatively, selectively permeable element 105 may comprise any porous material as described herein impregnated with one or more selectively permeable porous materials as described herein. In some non-limiting examples, the porous material may be impregnated with one or more selectively permeable porous materials via blending, knitting, injection, soaking, spraying, or a combination thereof.

It should be understood that, as described herein, the present disclosure is not particularly limited to the example shown in FIG. 1. In particular, a selectively permeable element as described herein may be provided at any point along the fluid path between, for example, ampoule 103 and a surface-contacting portion 106 of application member 102 of FIG. 1.

For example, in addition to or instead of having a pledget as described herein, applicator 100 may comprise an application member that comprises a selectively permeable porous material as described herein. In this way, application member 102 may function as both an application member as described herein and a selectively permeable element. Additionally or alternatively, application member 102 may comprise a foam and/or a felt as described herein having one or more selectively permeable elements thereon, such as one or more selectively permeable porous materials provided as a coating on at least one surface of the application member (including, but not limited to, surface-contacting portion 106). Additionally or alternatively, application member 102 may comprise a foam and/or a felt as described herein having one or more selectively permeable elements therein. For example, the foam and/or felt may be impregnated with one or more selectively permeable porous materials as described herein.

As described herein, the cleaning devices according to the present disclosure may comprise two, three, four, or more selectively permeable elements, wherein each of the selectively permeable elements is the same as or different from another selectively permeable element comprised by the cleaning device. For example, each selectively permeable element as described herein may independently be formed from a selectively permeable porous material as described herein. Additionally or alternatively, each selectively permeable element may independently comprise a porous material as described herein having one or more selectively permeable porous materials provided as a coating on at least one surface thereof. Additionally or alternatively, each selectively permeable element may independently comprise a porous material as described herein, the porous material being impregnated with one or more selectively permeable porous materials as described herein.

The at least one selectively permeable element according to the present disclosure is configured to selectively remove one or more selected components from a cleaning fluid passing therethrough, as described herein. Selective removal of one or more selected components from a cleaning fluid may be accomplished via one or more passes of the cleaning fluid through the at least one selectively permeable element, including but not limited to one or more passes via gravity-assisted laminar flow.

According to some aspects, the at least one selectively permeable element may be configured to selectively remove an amount of the one or more selected components sufficient to provide a cleaning fluid having an acceptable purity. As used herein, an "acceptable purity" may refer to a purity sufficient to comply with regulatory requirements. For example, an acceptably pure cleaning fluid may refer to a cleaning fluid as described herein having a concentration of impurities that is at or below a specified limit. In one non-limiting example, the at least one selectively permeable element may be configured to selectively remove an amount of PCA from a cleaning fluid such that the cleaning fluid has a PCA concentration of no more than about 150 ppm, optionally no more than about 100 ppm, and optionally no more than about 50 ppm. Additionally, or alternatively, the at least one selectively permeable element may be configured to selectively remove an amount of the one or more selected components from a cleaning fluid such that each of the one or more selected components is present in the cleaning fluid at a concentration of no more than about 1% w/v, optionally no more about 0.5% w/v, optionally no more than about 0.1% w/v, and optionally no more than about 0.05% w/v.

According to some aspects, the at least one selectively permeable element as described herein may be configured to provide a cleaning fluid having an extended shelf life. The extended shelf life may be provided at least by removing one or more impurities from the cleaning fluid as described herein. It should be understood that an extended shelf life may refer to a shelf life of a cleaning fluid contained in a cleaning device as described herein that is greater than a shelf life of the same cleaning fluid contained in a similar cleaning device that does not have a selectively permeable element as described herein.

As used throughout this application, the term "shelf life" refers to the length of time that a product (e.g., a cleaning fluid) may be stored while remaining within the specifications required for the form, fit, and function of the product. Shelf life may be determined by measuring certain characteristics of the product that may indicate that the product is unfit for medical use. For example, shelf life may be determined by measuring the concentration of impurities in the product after storage in long-term storage conditions. As used herein, the term "long-term storage conditions" refers to environmental conditions sufficient for a product to be acceptably stored for more than 72 hours. According to some aspects, long-term storage conditions may refer to a temperature of about 25° C. and a relative humidity of about 60%. Additionally or alternatively, shelf life may be determined by measuring the concentration of impurities in the product after storage at 37° C. and 65% relative humidity. Additionally or alternatively, shelf life may be determined by measuring the concentration of impurities in the product after storage at between about 15 and 30° C., with excursions at a temperature of no more than about 40° C.

The extended shelf life of the cleaning fluid may be 1 week, preferably 2 weeks, preferably 3 weeks, preferably 1 month, preferably 2 months, more preferably 3 months, more preferably 4 months, more preferably 5 months, more preferably 6 months, more preferably 7 months, more preferably 8 months, more preferably 9 months, more preferably 10 months, more preferably 11 months, more 12 months, preferably 13 months, more preferably 14 months, more preferably 15 months, more preferably 16 months, more preferably 17 months, more preferably 18 months, more preferably 19 months, more preferably 20 months, more preferably 21 months, more preferably 22 months, more preferably 23 months, more preferably 24 months, more preferably 25 months, more preferably 26 months, more preferably 27 months, more preferably 28 months, more preferably 29 months, more preferably 30 months, more preferably 31 months, more preferably 32 months, more preferably 33 months, more preferably 34 months, more preferably 35 months, and most preferably 36 months. According to some aspects, the extended shelf life may vary based on product presentation.

The present disclosure if also directed to methods of making a cleaning device herein. The method may comprise providing a body in selective fluid communication with an application member via a fluid path, wherein the application member is configured to apply a cleaning fluid to a surface. The method may further comprise providing at least one selectively permeable element along the fluid path sufficient to selectively remove one or more selected components from a cleaning fluid passing therethrough.

The present disclosure if also directed to methods of using a cleaning device as described herein. The method may comprise providing a cleaning device as described herein having a body containing a cleaning fluid, wherein the body is in selective fluid communication with an application member via a fluid path and wherein the application member is configured to apply the cleaning fluid to a surface. The fluid flow path may comprise at least one selectively permeable element as described herein. The method may comprise optionally contacting the cleaning fluid with resin particles as described herein in order to form one or more impurity complexes. The method comprises actuating the cleaning device such that the cleaning fluid travels along the fluid path and passes through the at least one selectively permeable element prior to application of the cleaning fluid to the surface via the application member.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The word "about" is used herein to mean within ±5% of the stated value, optionally within ±4%, optionally within ±3%, optionally within ±2%, optionally within ±1%, optionally within ±0.5%, optionally within 0.1%, and optionally within ±0.01%.

EXAMPLES

Example I: Selective Interaction Between Resin Particles and PCA in Alcoholic Solution of Chlorhexidine Gluconate First, a solution containing 2% (w/v) chlorhexidine gluconate (CHG) in about 70% (v/v) isopropyl alcohol and 30% (v/v) water was prepared. The solution was spiked with 4-chloroaniline (PCA) to a level of 100 ppm PCA. To 10 mL aliquots of this solution, 100 mg of a unique solid activated carbon test material was added. Specifically, each of the aliquots was treated with one of Sample 1, Sample 2, Sample 3, or Sample 4. Characteristics of Samples 1-4 are shown in Table 4 below.

TABLE 4

Activated Carbon Sample Characteristics

| | Sample 1 | Sample 2 | Sample 3 | Sample 4 |
|---|---|---|---|---|
| pH | neutral | neutral | 3 to 5 | 6 to 8 |
| Chlorides (Acid Ext.) | 0.05 mg/kg | 0.05 mg/kg | n/a | n/a |
| Iodine Number | 1600 | 1400 | n/a | n/a |
| Molasses Number EUR | 600 | 800 | 90 | 115 |
| Methylene Blue adsorption | 42 g/100 g | 34 g/100 g | 38 g/100 g | 34 g/100 g |
| Total Surface Area (B.E.T.) | 1700 $m^2/g$ | 1500 $m^2/g$ | 1850 $m^2/g$ | 1650 $m^2/g$ |
| Apparent density, tamped | 410 $kg/m^3$ | 460 $kg/m^3$ | 180 $kg/m^3$ | 260 $kg/m^3$ |
| Particle size, $D_5$ | 4 μm | 4 μm | 4 μm | 6 μm |
| Particle size, $D_{50}$ | 20 μm | 20 μm | 16 μm | 23 μm |
| Particle size, $D_{90}$ | 60 μm | 60 μm | 44 μm | 69 μm |
| Ash Content | 2% | 2% | 5% | 5% |
| Filtration Time | 35 min. | 35 min. | 30 min. | 14 min. |

Each of the mixtures was shaken for 30 minutes. Then, each sample was centrifuged, the resulting activated carbon was removed, and the supernatant was diluted according to the scheme required for direct injection into a High Pressure Liquid Chromatography (HPLC) instrument. One aliquot was not treated with activated carbon as a control.

Each sample was then analyzed via HPLC to determine the change in concentration of CHG and PCA. The results are shown in Table 5 below.

TABLE 5

PCA and CHG Reduction

| | PCA (ppm) | | % | CHG (% of original) | | % |
|---|---|---|---|---|---|---|
| Sample No. | Before Treatment | After Treatment | Reduction PCA | Before Treatment | After Treatment | Reduction CHG |
| Control | 100 | 100 | 0 | 100 | 100 | 0 |
| 1 | 100 | 34 | 66 | 100 | 86.8 | 13.2 |
| 2 | 100 | 19 | 81 | 100 | 72.3 | 27.7 |
| 3 | 100 | 66 | 34 | 100 | 77.3 | 22.7 |
| 4 | 100 | 67 | 33 | 100 | 80.4 | 19.6 |

As can be seen in Table 5, each sample surprisingly showed a reduction in PCA that was much greater than the reduction in CHG. It was thus determined that activated carbon selectively interacts more with PCA than CHG, thus allowing PCA to be selectively removed from a solution containing CHG in an organic environment.

What is claimed is:

1. A cleaning device comprising:

a body containing a cleaning fluid;

an application member in selective fluid communication with the body via a fluid path; and a first selectively permeably element provided along the fluid path, wherein the first selectively permeable element is configured to selectively interact with one or more selected components of the cleaning fluid sufficient to remove the one or more selected components from the cleaning fluid as the cleaning fluid travels along the fluid path, wherein selective interaction between the first selectively permeable element and the one or more selected components comprises at least a physical interaction, and wherein the one or more selected components comprises a chemical impurity.

2. The cleaning device according to claim 1, wherein the cleaning fluid is an organic solution.

3. The cleaning device according to claim 1, wherein the cleaning fluid comprises chlorhexidine gluconate, and wherein the chemical impurity comprises 4-chloroaniline.

4. The cleaning device according to claim 1, wherein the selective interaction between the first selectively permeable element and the one or more selected components further comprises a chemical interaction.

5. The cleaning device according to claim 4, wherein the chemical interaction comprises a pi-pi interaction.

6. The cleaning device according to claim 1, wherein the first selectively permeable element comprises a first selectively permeable porous material.

7. The cleaning device according to claim 6, wherein the first selectively permeable porous material has an average pore size of between about 4 Å and to 50 nm.

8. The cleaning device according to claim 6, wherein the first selectively permeable porous material comprises one or more organic functional groups.

9. The cleaning device according to claim 6, wherein the first selectively permeable porous material comprises activated carbon, a zeolite, or a combination thereof.

10. The cleaning device according to claim 9, wherein the first selectively permeable porous material comprises powdered activated carbon having a pH of between about 6.5 and 7.5.

11. The cleaning device according to claim 9, wherein the first selectively permeable porous material comprises powdered activated carbon having a total surface area (B.E. T.) of between about 1500 $m^2/g$ and 1850 $m^2/g$.

12. The cleaning device according to claim 9, wherein the first selectively permeable porous material comprises powdered activated carbon having a particle size distribution (D5) of between about 4 and 6 μm.

13. The cleaning device according to claim 9, wherein the first selectively permeable porous material comprises powdered activated carbon having a tamped apparent density of between about 180 $kg/m^3$ and 460 $kg/m^3$.

14. The cleaning device according to claim 9, wherein the first selectively permeable porous material comprises powdered activated carbon having a molasses number EUR of between about 90 and 800.

15. The cleaning device according to claim 6, wherein the first selectively permeable element is a pledget having a coating on at least one surface thereof, wherein the coating comprises the first selectively permeable porous material.

16. The cleaning device according to claim 6, wherein the first selectively permeable element is a pledget impregnated with the first selectively permeable porous material.

17. The cleaning device according to claim 6, wherein the first selectively permeable element is a pledget formed from the first selectively permeable porous material.

18. The cleaning device according to claim 6, wherein the first selectively permeable element is a coating on at least one surface of the application member, the coating comprising the first selectively permeable porous material.

19. The cleaning device according to claim 6, wherein the application member is impregnated with the first selectively permeable element, the first selectively permeable element comprising the first selectively permeable porous material.

20. A method for cleaning a surface, the method comprising:

providing a cleaning device comprising:

a body containing a cleaning fluid, an application member in selective fluid communication with the body via a fluid path, and a first selectively permeably element provided along the fluid path;

actuating the cleaning device such that the cleaning fluid travels from the body to the application member via the fluid path; and applying the cleaning fluid to a surface via the application member, wherein the first selectively permeable element is configured to selectively interact with one or more selected components of the cleaning fluid sufficient to remove the one or more selected components from the cleaning fluid as the cleaning fluid travels along the fluid path, and wherein selective interaction between the first selectively permeable element and the one or more selected components comprises at least a physical interaction, wherein the one or more selected components comprises a chemical impurity.

* * * * *